(12) United States Patent
Schuldt-Lieb et al.

(10) Patent No.: US 10,688,049 B2
(45) Date of Patent: Jun. 23, 2020

(54) PROCESS FOR THE PREPARATION OF A FREEZE-DRIED PHARMACEUTICAL COMPOSITION CONTAINING MITOMYCIN C

(71) Applicant: MEDAC GESELLSCHAFT FUR KLINISCHE SPEZIALPRAPARATE MBH, Wedel (DE)

(72) Inventors: Sonja Schuldt-Lieb, Hamburg (DE); Sebastian Bialleck, Hamburg (DE); Ingo Guhde, Hamburg (DE); Michaela Rehberg, Hamburg (DE)

(73) Assignee: MEDAC GESELLSCHAFT FÜR KLINISCHE SPEZIALPRÄPARATE MBH, Wedel (DE)

( * ) Notice: Subject to any disclaimer, the term of this patent is extended or adjusted under 35 U.S.C. 154(b) by 120 days.

(21) Appl. No.: 15/031,519

(22) PCT Filed: Oct. 16, 2014

(86) PCT No.: PCT/EP2014/072201
§ 371 (c)(1),
(2) Date: Apr. 22, 2016

(87) PCT Pub. No.: WO2015/059023
PCT Pub. Date: Apr. 30, 2015

(65) Prior Publication Data
US 2016/0256391 A1    Sep. 8, 2016

(30) Foreign Application Priority Data

Oct. 22, 2013  (EP) .................................... 13189775

(51) Int. Cl.
| | | |
|---|---|---|
| A61K 31/435 | (2006.01) | |
| A61K 9/19 | (2006.01) | |
| A61K 47/10 | (2017.01) | |
| A61K 31/407 | (2006.01) | |
| A61K 9/08 | (2006.01) | |
| A61K 9/16 | (2006.01) | |
| A61K 9/00 | (2006.01) | |
| A61K 47/18 | (2017.01) | |
| A61K 47/26 | (2006.01) | |

(52) U.S. Cl.
CPC .............. *A61K 9/19* (2013.01); *A61K 9/0019* (2013.01); *A61K 9/08* (2013.01); *A61K 9/1617* (2013.01); *A61K 9/1623* (2013.01); *A61K 9/1641* (2013.01); *A61K 31/407* (2013.01); *A61K 47/10* (2013.01); *A61K 47/18* (2013.01); *A61K 47/26* (2013.01)

(58) Field of Classification Search
CPC ............................... A61K 31/435; B01J 37/32
See application file for complete search history.

(56) References Cited

U.S. PATENT DOCUMENTS 5,216,011 A * 6/1993 Paborji ................ A61K 9/0019
                                                                514/410
2009/0162440 A1    6/2009 Xiaoping et al.

FOREIGN PATENT DOCUMENTS

| CN | 1712014 A | 12/2005 |
|---|---|---|
| CN | 101204382 A | 6/2008 |
| DE | 19957371 A1 | 6/2001 |
| EP | 0 782 850 A1 | 7/1997 |
| GB | 830874 | 3/1960 |
| GB | 2 171 408 A | 8/1986 |
| JP | 2005-518434 | 6/2005 |
| WO | 03/072082 | 9/2003 |

OTHER PUBLICATIONS

CN101204382 (A)—Jun. 25, 2008. Machine translation. (Year: 2008).*
CN1712014 (A)—Dec. 28, 2005. Machine Translation. (Year: 2005).*
Wittaya-Areekul ("Freeze-drying of tert-butyl alcohol/water cosolvent systems: effects of formulation and process variables on residual solvents." J Pharm Sci. Apr. 1998;87(4):491-5.) (Year: 1998).*
Wakaki et al., "Isolation of New Fractions of Antitumor Mitomycins," Antibiotics and Chemotherapy, vol. 8, No. 5, pp. 228-240, 269-270, MD Publications, Inc., New York, NY, 1958.
Underberg et al., "Stereoselectivity in the Mechanism of Acid Hydrolysis of Mitomycins," Chem. Pharm. Bull. 1987, 35(11), 4557-4561.

* cited by examiner

*Primary Examiner* — Jeffrey S Lundgren
*Assistant Examiner* — Chris E Simmons
(74) *Attorney, Agent, or Firm* — Hovey Williams LLP

(57) ABSTRACT

A process is described for the preparation of freeze-dried pharmaceutical compositions of mitomycin C, which are characterized by high stability and can be rapidly reconstituted to form solutions.

7 Claims, No Drawings

PROCESS FOR THE PREPARATION OF A FREEZE-DRIED PHARMACEUTICAL COMPOSITION CONTAINING MITOMYCIN C

RELATED APPLICATIONS

This application claims priority to PCT International Patent Application No. PCT/EP2014/072201, filed Oct. 16, 2014, which claims the priority benefit of EP Patent Application No. 13189775.3, filed Oct. 22, 2013, both of which are hereby incorporated by reference in their entirety.

The invention relates to a process for the preparation of a freeze-dried pharmaceutical composition containing mitomycin C, which is characterized by high stability and purity and can rapidly be reconstituted to form ready-to-use solutions.

Mitomycin C, chemical name (1aS,8S,8aR,8bS)-6-amino-8-[[(aminocarbonyl)oxy]methyl]-1,1a,2,8,8a,8b-hexahydro-8a-meth-oxy-5-methyl-azirino[2',3T:3,4]pyrrolo[1,2-a]indol-4,7-dione or 6-amino-8a-methoxy-5-methyl-4,7-dioxo-1,1a,2,4,7,8,8a,8b-octahydroazarino[2'-,3":3,4]pyrrolo[1,2-a]indol-8-ylmethyl carba-mate, was first isolated in 1958 from *Streptomyces caespitosus*(see Wakaki et al., Antibiotics and Chemotherapy, 8, 228, 1958 and GB 830874). It has excellent antitumour activity and can above all be used for the treatment of bladder tumours, gastric carcinomas, bronchial carcinomas, pancreatic carcinomas, colorectal carcinomas, mammary carcinomas, liver cell carcinomas, cervical carcinomas, oesophageal carcinomas, carcinomas in the head and neck region, chronic myeloid leukaemia and osteosarcoma. For this, it is used in the form of aqueous solutions for injection or infusion or solutions for intravesicular use.

U.S. Pat. No. 5,216,011 describes solutions of mitomycin C which can for example be administered by injection. These solutions are intended to circumvent difficulties in the preparation of freeze-dried preparations. As solvent, the solutions comprise 40 to 100 vol.-% propylene glycol and 0 to 60 vol.-% water.

Further, from DE 199 57 371 an aqueous solution of mitomycin C is known, which comprises buffer and has a pH in the range from 6.0 to 9.0. In addition, the solution is characterized by a specific ratio of mitomycin C concentration to buffer ionic strength.

However, the shelf life of ready-to-use solutions of mitomycin is not sufficient, since the active substance content decreases markedly on storage. For this reason, mitomycin C is prepared in the form of lyophilisates or dry powders, and these pharmaceutical forms are reconstituted with sterile solvent directly before administration, so as to give ready-to-use solutions. Lyophilisates are marketed for example under the brand name "Mitem". Dry powders, for example mixed with NaCl, are for example obtainable under the brand name "Mito-medac".

However, the lyophilisates available on the market have the disadvantage that only a relatively short shelf life of at most two years is stated for them. This is due to the high instability of mitomycin C, which readily decomposes in the lyophilisation solution with formation of a range of degradation products. The main degradation products are albomitomycin C, D1 and D2, the structural formulae of which are reproduced below together with that of mitomycin C.

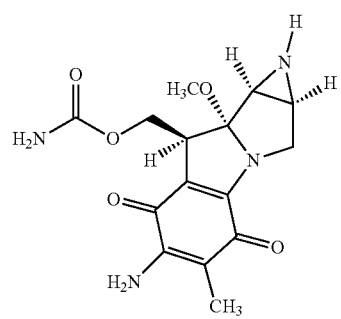

Mitomycin C

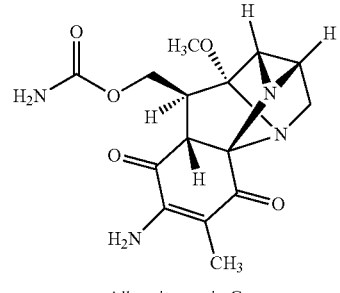

Albomitomycin C

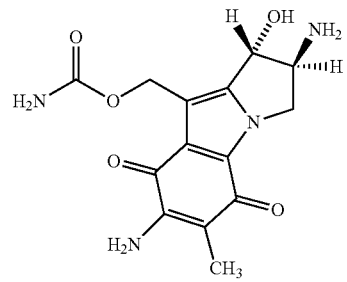

D1

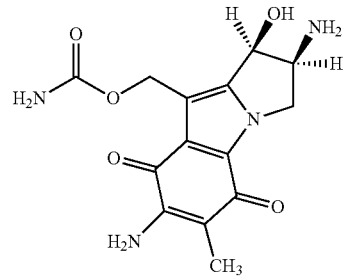

D2

Although dry powders of mitomycin C have a longer shelf life of about four years, they have the disadvantage that during their preparation dusts are formed which result in health-endangering contamination of the personnel and contamination of the production plants. The long period of time necessary for complete dissolution of these dry powders is also not satisfactory.

With the known lyophilisates and dry powders, the reconstitution to solutions is usually effected to give end concentrations of 1 mg/ml mitomycin C, e.g. 20 mg mitomycin C to 20 ml water or isotonic saline solution (0.9% wt.-%). Lower concentrations after dilution to 0.2 and 0.15 mg/ml for ophthalmological applications are also known. However, because of the poor solubility of the known products, a higher end concentration in water is not possible. In the literature, their saturation concentration is stated as 0.5-1.0 mg/ml.

The object of the invention is therefore to avoid the disadvantages of the known lyophilisates and dry powders, and in particular to provide a process for the preparation of a freeze-dried pharmaceutical composition of mitomycin C, which process does not result in a significant reduction in the active substance content and which results in a composition which has high stability and purity and hence exhibits only slight degradation of the active substance even on prolonged storage. In addition, the pharmaceutical composition produced should be rapidly and completely reconstitutable to form ready-to-use solutions which can have a high concentration of active substance.

This object is achieved by the process according to claims 1 to 14. Also a subject of the invention is the freeze-dried pharmaceutical composition according to claims 15 to 19 and the mitomycin C-containing solution according to claims 20 and 21.

The process according to the invention for the preparation of a freeze-dried pharmaceutical composition comprising mitomycin C is characterized in that a solution of mitomycin C is freeze-dried, wherein the solution comprises at least one organic solvent.

The solution subjected to the freeze-drying in the process is also referred to below as "lyophilisation solution".

The organic solvent used in the process according to the invention is in particular selected from the group comprising tert.-butanol, n-propanol, n-butanol, isopropanol, ethanol, methanol, 1-pentanol, chlorobutanol, acetic acid, acetone, dimethyl carbonate, acetonitrile, dichloromethane, methyl ethyl ketone, methyl isobutyl ketone, methyl acetate, carbon tetrachloride, dimethyl sulphoxide, N,N-dimethylacetamide, hexafluoroacetone, dimethyl sulphone and cyclohexane. The organic solvent is preferably selected from the group of tert.-butanol, ethanol, isopropanol, acetone, dimethyl sulphoxide and N,N-dimethylacetamide. Particularly preferably, the organic solvent is tert.-butanol.

In one embodiment, the organic solvent is the only solvent in the solution. When organic solvents which are solid at room temperature are used, the mitomycin C is usually dissolved in previously melted organic solvent.

In a further, preferred embodiment, the solution used in the process according to the invention also comprises water.

The dissolution of mitomycin C in at least one organic solvent, preferably in a mixture with water, surprisingly results in a lyophilisation solution which is physically and chemically stable at room temperature for up to 48 h and at 5° C. even up to 9 days. At the same time, the content of impurities in this solution also remains surprisingly low and thus the purity of the solution remains very high. Because of the high stability and the high purity of the solution, very pure freeze-dried compositions of mitomycin C can be prepared with the process according to the invention.

The freeze-drying of this solution surprisingly results in no significant increase in impurities, so that the freeze-dried composition obtained also exhibits high purity. The composition also surprisingly exhibits very high stability and even after storage for several months it exhibits a high content of active substance and only small quantities of undesired degradation products.

Further, the composition produced with the process according to the invention, also referred to below as "lyophilisate", exhibits a surprisingly high solubility in the solvents usually used for reconstitution and enables the preparation of ready-to-employed solutions which comprise mitomycin C at a concentration of more than 1 mg/ml.

Hence, by using the composition, ready-to-use solutions with a particularly high active substance concentration can be produced.

The solution used in the process according to the invention preferably comprises a mixture of ethanol and water, a mixture of isopropanol and water, a mixture of acetone and water, a mixture of dimethyl sulphoxide and water, or a mixture of dimethyl sulphoxide and dimethylacetamide. Particularly preferably the solution comprises a mixture of tert.-butanol and water.

The mixture of ethanol and water used in particular comprises at least 1 wt.-%, preferably at least 5 wt.-%, particularly preferably at least 10 wt.-% and quite particularly preferably at least 15 wt.-% ethanol.

The mixture of isopropanol and water used in particular comprises at least 1 wt.-%, preferably at least 5 wt.-%, particularly preferably at least 10 wt.-% and quite particularly preferably at least 15 wt.-% isopropanol.

The mixture of acetone and water used in particular comprises at least 1 wt.-%, preferably at least 5 wt.-%, particularly preferably at least 10 wt.-% and quite particularly preferably at least 15 wt.-% acetone.

The mixture of dimethyl sulphoxide and water used in particular comprises at least 1 wt.-%, preferably at least 30 wt.-%, particularly preferably at least 50 wt.-% and quite particularly preferably at least 80 wt.-% dimethyl sulphoxide.

The mixture of dimethyl sulphoxide and dimethylacetamide used in particular comprises at least 5 wt.-% and preferably at least 50 wt.-% dimethyl sulphoxide.

In the process according to the invention, a solution which comprises a mixture of tert.-butanol and water is particularly preferably used. This mixture of tert.-butanol and water in particular comprises at least 1 wt.-%, preferably at least 5 wt.-%, particularly preferably at least 10 wt.-% and more preferably at least 15 wt.-% tert.-butanol.

In a quite particularly preferred embodiment, the mixture of tert.-butanol and water used comprises 80 to 99 wt.-%, in particular 84 to 95 wt.-%, preferably 88 to 92 wt.-% and quite particularly preferably about 89 wt.-% tert.-butanol. In an alternative quite particularly preferred embodiment, the mixture of tert.-butanol and water used comprises 10 to 30 wt.-%, in particular 15 to 25 wt.-%, preferably 18 to 22% and quite particularly preferably about 20 wt.-% tert.-butanol.

The lyophilisation solution used in the process according to the invention usually comprises mitomycin C at a concentration of 0.1 to 500 mg/g, in particular 0.5 to 10.0 mg/g, preferably 0.8 to 6.0 mg/g and particularly preferably 1.0 to 4.0 mg/g.

It is preferable that the solution also comprises at least one additive selected from the group of urea, polyethylene glycol and mannitol. By means of these additives, lyophilisates can be prepared which have particularly high solubility in solvents used for reconstitution. The use of these additives inert towards the active substance results in a lyophilisate which, because of its special properties, protects the active substance against destabilizing influences and thus preserves the active substance in its pure form.

In a preferred embodiment of the process according to the invention, the solution comprises urea at a concentration of 1 to 200 mg/g, in particular 5 to 100 mg/g and preferably 10 to 60 mg/g.

The polyethylene glycol has in particular an average molecular weight (number average) of 1000 to 8000 and preferably of 2000 to 8000. Particularly preferably, PEG 4000, which has an average molecular weight (number average) of about 4000, is used as polyethylene glycol.

In a preferred embodiment of the process according to the invention, the solution comprises polyethylene glycol at a concentration of 1 to 200 mg/g, in particular 5 to 100 mg/g and preferably 10 to 60 mg/g.

In a preferred embodiment of the process according to the invention, the solution comprises mannitol at a concentration of 1 to 200 mg/g, in particular 5 to 100 mg/g and preferably 10 to 60 mg/g.

The solution can additionally also comprise other usual additives such as further sugar alcohols, e.g. isomalt, lactitol, sorbitol, lactitol, sorbitol, xylitol, threitol, erythritol or arabitol, sugars, e.g. sucrose, glucose, fructose, maltose, rhamnose, lactose or trehalose, amino acids, e.g. L-phenylalanine, L-tryptophan, L-proline, L-histidine, L-glycine or L-arginine, polymers, e.g. polyvinylpyrrolidones, polyvinyl acetates, starch derivatives, e.g. cyclodextrins, dextroses, amylopectins, amyloses, polysaccharides, e.g. alginates, pectins, celluloses, agents for adjusting isotonicity, e.g. sodium chloride, calcium chloride dihydrate, sodium acetate trihydrate, disodium hydrogen phosphate dihydrate, and/or agents for adjusting the pH, e.g. trometamol, usually at concentrations in each case of 1 to 200, in particular 5 to 100 and preferably 10 to 60 mg/g.

The freeze-drying of the lyophilisation solution is as a rule effected using freeze-drying processes and machines normally used for pharmaceutical purposes. As a rule, the solution is filled into a suitable vessel, and the vessel is placed in a conventional freeze-dryer with coolable and heatable surfaces on which the solution can be exposed to the various temperatures of the freeze-drying process. To achieve the drying, the solution is usually frozen and exposed to a decreased atmospheric pressure. As a result, sublimation of the solvent from the frozen solution takes place to a great extent, which precipitates for example on cooler regions of the freeze-dryer provided for this. This is then as a rule also followed by a secondary drying at higher temperatures. After completion of the freeze-drying, the lyophilisate obtained is as a rule allowed to come to room temperature and the vessel used is sealed under sterile conditions. A suitable programme for the lyophilisation can comprise charging of the vessel at room temperature, freezing at −50° C. to −35° C. under normal pressure, subsequent lowering of the atmospheric pressure and then increasing of the temperature by 25 to 95° C. in order to effect the drying.

The freeze-dried composition obtained with the process according to the invention evidently also has a special and advantageous structure, since only a very short period of less than 60 seconds, in particular less than 30 seconds and preferably 4 to 20 seconds suffices for complete reconstitution to form a ready-to-use solution. This is an important advantage, since as a result it is possible for clinic staff to prepare ready-to-use solutions freshly directly before the intended administration to patients, without having to allow for long waiting times for complete dissolution. Likewise, with such short reconstitution times, the risk of undesired degradation reactions of the active substance decreases.

For the reconstitution of the composition, isotonic saline solution or water for injection is usually employed. Other pharmaceutically acceptable solutions are also possible for the reconstitution, such as for example Ringer's lactate solutions or phosphate buffers.

Because of the described advantageous properties, the invention also relates to a freeze-dried pharmaceutical composition comprising mitomycin C, wherein the composition is obtainable by the process according to the invention.

The composition according to the invention preferably comprises at least one additive selected from the group of urea, polyethylene glycol and mannitol. Such a composition requires smaller quantities of reconstituting agent for reconstitution and thus a ready-to-use solution with a particularly high concentration of mitomycin C can be prepared by means thereof.

The composition usually comprises urea at a concentration of 0.2 to 1, in particular 0.5 to 0.99, preferably 0.8 to 0.95 and particularly preferably 0.93 to 0.94 g per gram of composition.

The composition usually comprises polyethylene glycol at a concentration of 0.2 to 1, in particular 0.5 to 0.99, preferably 0.8 to 0.95 and particularly preferably 0.93 to 0.94 g per gram of composition.

The composition usually comprises mannitol at a concentration of 0.2 to 1, in particular 0.5 to 0.99, preferably 0.8 to 0.95 and particularly preferably 0.93 to 0.94 g per gram of composition.

The composition according to the invention comprises the impurities D1, D2 and albomitomycin C in a total quantity of in particular less than 2.0%, preferably less than 1.5%, particularly preferably less than 1.0%, more preferably less than 0.8% and quite particularly preferably less than 0.6%, wherein the quantity of these impurities is determined according to the impurities process according to Ph Eur 8.0 Mitomycin Monograph 01/2008: 1655. In the examples, this determination process is also referred to as process 4.

Because of the aforementioned advantageous properties, the invention also relates to a mitomycin C-containing solution for freeze-drying which comprises at least one organic solvent selected from the group of tert.-butanol, n-propanol, n-butanol, isopropanol, ethanol, methanol, 1-pentanol, chlorobutanol, acetic acid, acetone, dimethyl carbonate, acetonitrile, dichloromethane, methyl ethyl ketone, methyl isobutyl ketone, methyl acetate, carbon tetrachloride, dimethyl sulphoxide, dimethylacetamide, hexafluoroacetone, dimethyl sulphone and cyclohexane.

The organic solvent is preferably selected from the group of tert.-butanol, ethanol, isopropanol, acetone, dimethyl sulphoxide and N,N-dimethylacetamide and particularly preferably the organic solvent is tert.-butanol.

The preferred embodiments for the solution used stated above in the description of the process according to the invention are also preferred for the solution according to the invention.

As already described above, the solution according to the invention is in particular characterized in that the active substance in it is very stable and almost no formation of impurities occurs.

The invention is explained in more detail below on the basis of examples.

EXAMPLES

Example 1

Solubility and Stability of Mitomycin C in Various Solvents

The solubility and stability of mitomycin C in the various solvents and solvent mixtures stated in Table 1 were investigated.

TABLE 1

"Solvents/solvent mixtures used"

| No. | Co-solvent wt.-% | Water wt.-% | Mitomycin C concentration [mg/g] | Mannitol concentration [mg/g] |
|---|---|---|---|---|
| 1 | Water | — | 100 | 2.0 | 4.0 |
| 2 | Tert.-butanol | 32.6 | 67.4 | 2.1 | 4.1 |
| 3 | Ethanol | 16.4 | 83.6 | 2.2 | 4.4 |
| 4 | Isopropanol | 16.2 | 83.8 | 2.2 | 4.3 |
| 5 | Acetone | 7.1 | 92.9 | 2.0 | 4.1 |

For this purpose, solutions which contained 2.0 to 2.2 mg/g mitomycin C and 4.0 to 4.4 mg/g mannitol were prepared using each of these mixtures.

After 1.5 hours' stirring time at room temperature and with exclusion of light, the mixtures obtained were examined for particles under irradiation with linearly polarized light. The result of the visual examination is presented in Table 2.

TABLE 2

"Visual examination"

| No. | Solvent/solvent mixture wt.-% | Description of the mixtures |
|---|---|---|
| 1 | Water 100% | dark blue suspension, not completely dissolved |
| 2 | Tert.-butanol 32.6% | dark blue clear solution, completely dissolved |
| 3 | Ethanol 16.4% | dark blue clear solution, completely dissolved |
| 4 | Isopropanol 16.2% | dark blue clear solution, completely dissolved |
| 5 | Acetone 7.1% | dark blue clear solution, completely dissolved |

Further, the content of mitomycin C and impurities in the mixtures obtained was determined after 24 hours' storage at room temperature. The corresponding results are presented in Table 3.

TABLE 3

"Content of mitomycin C and impurities after 24 h storage at room temperature"

| No. | Solvent mixture wt.-% | Mitomycin C content [%]* | Total content of impurities (D1, D2 and albomitomycin C) [%]** |
|---|---|---|---|
| 2 | Tert.-butanol 32.6% | 98.04 | 1.96 |
| 3 | Ethanol 16.4% | 94.74 | 5.26 |
| 4 | Isopropanol 16.2% | 95.69 | 4.30 |
| 5 | Acetone 7.1% | 93.99 | 6.01 |

*Determination by process 1 (see Table 5)
**Determination by process 2 (see Table 5)

The results presented in Table 3 show that the mitomycin C in the lyophilisation solution in a mixture of tert.-butanol and water used according to the invention has particularly high stability.

Further, the mixtures obtained were again examined for visible particles under irradiation with linearly polarized light after 24 hours' storage with exclusion of light at (a) room temperature and (b) 2 to 8° C. The results thus obtained are presented in Table 4.

TABLE 4

"Visual examination after storage for 24 h"

| No. | Solvent/solvent mixture wt.-% | Storage at room temperature | Storage at 2 to 8° C. |
|---|---|---|---|
| 1 | Water 100% | dark blue suspension; dispersed particles | dark blue suspension |
| 2 | Tert.-butanol 32.6% | dark blue clear solution | dark blue clear solution |
| 3 | Ethanol 16.4% | dark blue clear solution; needle-like particles | dark blue clear solution; needle-like particles |
| 4 | Isopropanol 16.1% | dark blue clear solution | dark blue clear solution; needle-like particles |
| 5 | Acetone 7.1% | dark blue clear solution; needle-like particles | dark blue clear solution; needle-like particles |

With the solvent mixtures usable according to the invention, markedly more stable solutions were obtained than with water. The solution obtained with the mixture of 32.6 wt.-% tert.-butanol and 67.4 wt.-% water proved to be the most stable, since no particles were visible in it even after 24 h both at room temperature and also at 2 to 8° C. Furthermore, in the tert-butanol-water mixture after 24 hours' storage at room temperature the content of mitomycin C was the highest and the content of impurities the lowest.

Determination of the Content of Mitomycin C and of Impurities by High Pressure Liquid Chromatography The samples are each diluted to 0.5 mg/ml mitomycin C with N,N-dimethylacetamide. The reference solution contains 0.5 mg/ml mitomycin C in N,N-dimethylacetamide.

TABLE 5

"High pressure liquid chromatography conditions"

| | Process 1 | Process 2 |
|---|---|---|
| Detection: | UV at 365 nm | UV at 254 nm |
| Mobile phase: | Buffer/methanol 62.5/37.5, vol/vol | Buffer/methanol 75/25, vol/vol |
| | Buffer: | Buffer: |
| | 0.025% acetic acid in 0.02M ammonium acetate | 0.025% acetic acid in 0.02M ammonium acetate |
| Flow rate: | 1.4 ml/min | 2.6 ml/min |

Column: YMC-Pack Phenyl 4.6 mm×300 mm, 10 µm

Temperature: 25° C.

Injection volume: 10 µl

Example 2

Solubility and Stability of Mitomycin C in Dimethyl Sulphoxide and a Mixture of Dimethyl Sulphoxide and N,N-Dimethylacetamide The solubility and stability of mitomycin C in the solvents stated in Table 6, namely in dimethyl sulphoxide (DMSO) and a mixture of dimethyl sulphoxide (DMSO) and N,N-dimethylacetamide (DMAA) were investigated.

TABLE 6

"DMSO or DMSO/DMAA as solvent/solvent mixture"

| No. | Dimethyl sulphoxide wt.-% | N,N-Dimethylacetamide wt.-% |
|---|---|---|
| 6 | 5.7 | 94.3 |
| 7 | 100 | — |

For this purpose, solutions using each of these solvents were prepared, which for No. 6 (DMSO/DMAA) contained 0.53 mg/g mitomycin C and 8.0 mg/g urea and for No. 7 (DMSO) 1.82 mg/g mitomycin C and 27.3 mg/g urea. The solutions were stored at room temperature and with exclusion of light for a period of up to 71.5 hours.

TABLE 7a

"Content of mitomycin in DMSO/DMAA mixture"

| DMSO/DMAA wt.-% | Mitomycin content [%] | | | | | |
|---|---|---|---|---|---|---|
| | t = 0 | t = 6.5 h | t = 14.5 h | t = 21 h | t = 42 h | t = 71.5 h |
| 5.7/94.3[1] | 100 | 99.93 | 99.62 | 98.84 | 99.11 | 98.58 |

[1]Content determined with process 3

TABLE 7b

"Purity of mitomycin in DMSO"

| DMSO wt.-% | Mitomycin purity [%] | | | | | |
|---|---|---|---|---|---|---|
| | t = 0 | t = 4 h | t = 6.5 h | t = 13 h | t = 20 h | t = 26.5 h |
| 100[2] | 100 | 99.31 | 99.32 | 99.19 | 99.36 | 99.32 |

[2]Purity determined with process 4; purity is defined as area of the mitomycin peak relative to the total area of all peaks in the HPLC chromatogram In both solvents, the mitomycin C proved to be very stable. The use of DMSO alone resulted in a particularly small decrease in the original content of mitomycin C from 100% to 99.32% within a period of 26.5 hours.

The content of mitomycin C and hence the stability of the solutions obtained was checked by processes 3 and 4. Process 3 corresponds to the content process according to Ph Eur 8.0 Mitomycin Monograph 01/2008: 1655. Process 4 corresponds to the impurities process according to Ph Eur 8.0 Mitomycin Monograph 01/2008: 1655.

Example 3

Solubility and Stability of Mitomycin C in Various Tert.-Butanol/Water Mixtures

The solubility and stability of mitomycin C in the various mixtures of tert.-butanol and water stated in Table 8 were investigated.

For this purpose, solutions using each of these mixtures were prepared, wherein the concentration of mitomycin C was 2.1 mg/g for mixture No. 8, 2.2 mg/g for mixture No. 9 and 2.4 mg/g for mixture No. 10.

These were stored for 16 h with exclusion of light at (a) room temperature and (b) at 2 to 8° C. and then again examined for visible particles under irradiation with linearly polarized light. The results thus obtained are also presented in Table 8.

TABLE 8

"Visual examination after storage for 16 h"

| No. | Solvent mixture wt.-% | Storage at room temperature (a) | Storage at 2 to 8° C. (b) |
|---|---|---|---|
| 8 | tert.-butanol 32.6% | dark blue clear solution | dark blue clear solution |
| 9 | tert.-butanol 51.7% | dark blue clear solution | dark blue clear solution |
| 10 | tert.-butanol 72.9% | dark blue clear solution | dark blue clear solution |

All mixtures of tert.-butanol and water were capable of dissolving the stated quantity of mitomycin C, and in the solutions obtained no particles were visible even after 16 h storage.

For the HPLC determination of the stability of mitomycin C in tert.-butanol/water mixtures, mitomycin C was added to a mixture of 20 wt.-% tert.-butanol and 80 wt.-% water (No. 11) in a quantity such as to obtain a solution with a concentration of 10 mg/g mitomycin C. Further, mitomycin C was added to a mixture of 32.6 wt.-% tert.-butanol and 67.4 wt.-% water (No. 12) in a quantity such as to obtain a solution with a concentration of 2.1 mg/g mitomycin C. Further, mitomycin C was added to a mixture of 89 wt.-% tert.-butanol and 11 wt.-% water (No. 13) in a quantity such as to obtain a solution with a concentration of 5 mg/g mitomycin C. Further, a mitomycin-compriseing solution in pure tert.-butanol (100 wt.-%) (No. 14) and for comparison a solution in water (No. 15) were prepared. In the experiment with pure tert.-butanol, this was firstly melted by warming to about 30° C. and the mitomycin C was then dissolved in the melt.

The solutions were then stored for 24 h at room temperature in brown glass vessels. The respective results are presented in Table 9.

TABLE 9

"Stability of mitomycin C in tert.-butanol/water mixtures"

| No. | Solvent mixture wt.-% | Mitomycin [mg/g] | Mitomycin purity* t = 0 h [%] | Mitomycin purity* t = 6 h [%] | Mitomycin purity* t = 24 h [%] |
|---|---|---|---|---|---|
| 11 | Tert.-butanol 20% | 10 | 99.51 | 97.01 | 93.55 |
| 12 | Tert.-butanol 32.6% | 2.1 | 100.0 | 99.4 | 98.7 |
| 13 | Tert.-butanol 89% | 5 | 99.56 | 98.95 | 98.47 |
| 14 | Tert.-butanol 100% | 0.38 | 100.0 | 100.0 | 100.0 |
| 15 | Water (Reference) | 0.48 | 96.8 | 92.1 | 89.9 |

*HPLC determination by process 2; purity is defined as area of the mitomycin peak relative to the total area of all peaks in the HPLC chromatogram In the tert.-butanol-containing solutions, the mitomycin C had high stability, wherein the use of the mixtures No. 12 and No. 13 resulted in a particularly slight decrease in the original purity at t=0 of mitomycin C from 100.0% to 98.7% and 99.56% to 98.47%. A particularly high purity of 100.0 wt.-% after 24 h could be achieved in 100 wt.-% tert.-butanol, however, the solubility of mitomycin C in pure tert.-butanol is lower.

In contrast to this, the purity of mitomycin C in water after 24 h is significantly worse (at t=0 from 96.8% to 89.9%).

Example 4

Compatibility of Further Additives with Tert.-Butanol/Water Mixtures

Several solutions were prepared, each by dissolving 20 mg mitomycin C in 6 g of a mixture of 89 wt.-% tert. butanol and 11 wt.-% water. The additives urea, PEG 4000 or trometamol were added to these solutions, in order in each case to give a concentration of 50 mg/g. In addition, the solution with trometamol was adjusted to a pH of 7.4 with acetic acid.

At t=0 and after 6 h and 24 h at room temperature, the solutions were examined for their content of mitomycin C and compared with a solution which contained no further additive. The determination of the content was performed according to process 2, and the results are presented in Table 10.

TABLE 10

"Stability of solutions with urea, polyethylene glycol and trometamol"

| Additive | Mitomycin C purity* t = 0 | Mitomycin C purity* t = 6 h | Mitomycin C purity* t = 24 h |
|---|---|---|---|
| Urea | 99.69 | 99.76 | 99.14 |
| PEG 4000 | 100 | 99.58 | 99.50 |
| Trometamol | 99.56 | 99.44 | 99.50 |
| Without additive | 99.61 | 99.63 | 99.48 |

*HPLC determination by process 2; purity is defined as area of the mitomycin peak relative to the total area of all peaks in the HPLC chromatogram

Example 5

Stability of Mitomycin C in Urea-Containing Tert Butanol/Water Mixtures

Urea was dissolved in a mixture of 89 wt.-% tert.-butanol and 11 wt.-% water in a quantity such as to achieve a concentration of 5 wt.-%. Next, mitomycin C was added in a quantity such as to obtain a concentration of 3.33 mg/g, and the solution was stirred for one hour. The solution was filled into brown glass vessels and stored for 9 days at room temperature (RT) without protection against light, at room temperature (RT) with exclusion of light and at 5° C. with exclusion of light.

Purity determinations according to process 2 were performed at different times. The results are presented in Table 11.

TABLE 11

"Stability of mitomycin solutions with urea"

| Storage | Mitomycin purity* [%] | | | | | |
|---|---|---|---|---|---|---|
| | t = 0 | t = 6 h | t = 24 h | t = 48 h | t = 72 h | t = 9 d |
| RT; without protection against light | 99.32 | 98.83 | 97.60 | 96.77 | 96.14 | 95.78 |
| RT; with exclusion of light | 99.33 | 98.83 | 97.80 | 97.04 | 96.74 | 96.35 |
| 5° C.; with exclusion of light | 99.23 | 99.18 | 99.20 | 98.86 | 98.80 | 98.21 |

*HPLC determination by process 2; purity is defined as area of the mitomycin peak relative to the total area of all peaks in the HPLC chromatogram Even after nine days' storage, under all conditions, the solution was still surprisingly stable and the purity of the solution surprisingly high.

Example 6

Freeze-Drying of Solutions of Mitomycin C in Various Tert.-Butanol/Water Mixtures Firstly, solutions of mitomycin C in mixtures of tert.-butanol and water with 16.1 wt.-%, 32.6 wt.-% and 72.9 wt.-% tert.-butanol were prepared. These solutions contained 2.1 mg/g mitomycin C and 4.1 mg/g mannitol for the solution with the mixture with 16.1 wt.-% tert.-butanol, 2.2 mg/g mitomycin C and 4.3 mg/g mannitol for the solution with the mixture with 32.6 wt.-% tert.-butanol and 2.4 mg/g mitomycin C and 4.8 mg/g mannitol for the solution with the mixture with 72.9 wt.-% tert.-butanol.

All solutions were clear and sufficiently stable.

For comparison, a solution of mitomycin C in water, which contained 7 mg/g mannitol and because of the poor solubility in water 0.7 mg/g mitomycin C, was also prepared.

By conventional freeze-drying with (i) freezing of the solutions, (ii) application of a vacuum, (iii) primary and (iv) secondary drying, lyophilisates were obtained. These were reconstituted with water, and the reconstituted solutions obtained were analysed according to Example 1 for their content of mitomycin C and of impurities. The results are presented in Table 12.

TABLE 12

"Content of mitomycin C and impurities after freeze-drying and reconstitution"

| Quantity of tert.-butanol in mixture wt.-% | Mitomycin C Content** [%] | Impurities Content*** [%] Total; D1; D2; albomitomycin C |
|---|---|---|
| Tert.-butanol 0% | 98.36 | 1.64; 0.40; 0.48; 0.76 |
| Tert.-butanol 16.1% | 99.55 | 0.46; ND*; 0.15; 0.31 |
| Tert.-butanol 32.6% | 99.81 | 0.20; ND*; 0.10; 0.10 |
| Tert.-butanol 72.9% | 100.00 | ND*; ND*; ND*; ND* |

*ND = not detectable, i.e. below the detection limit
**HPLC determination by process 1
***HPLC determination by process 2

After lyophilisation and reconstitution, all mixtures of tert.-butanol and water used according to the invention resulted in solutions with a very high content of mitomycin C and only a very low content of impurities (D1, D2 and albomitomycin C).

In contrast to this, lyophilisation using water gave a reconstituted solution with a markedly lower content of mitomycin C and a very significant quantity of impurities.

Example 7

Stability of Mitomycin C in Tert.-Butanol-Water Mixture (89/11) with 20 mg/g Urea Solutions of mitomycin C in a mixture of 89 wt.-% tert.-butanol and 11 wt.-% water were prepared. As well as 1.33 mg/g mitomycin C, the solutions also each contained 20 mg/g urea. At t=0 and after 5, 22 and 27 hours at room temperature (RT) with exclusion of light and in the refrigerator, the purity of the solutions was investigated according to process 2. The results are shown in Table 13.

TABLE 13

"Stability of mitomycin C in 20 mg/g urea-containing solutions"

| | Mitomycin C purity* [%] | | |
|---|---|---|---|
| Conditions | t = 5 h | t = 22 h | t = 27 h |
| RT; with exclusion of light | 99.7 | 99.2 | 98.9 |
| 5° C.; with exclusion of light | 99.8 | 99.8 | 99.7 |

*HPLC determination by process 2; purity is defined as area of the mitomycin peak relative to the total area of all peaks in the HPLC chromatogram Even after more than one day's storage at room temperature, the purity of the solution is surprisingly high, which reflects the surprisingly high stability of the active substance in the solvent.

Example 8

Stability of Mitomycin C in Tert.-Butanol-Water Mixture (89/11) with 25 mg/g Urea Solutions of mitomycin C in a mixture of 89 wt.-% tert.-butanol and 11 wt.-% water were prepared. As well as 1.67 mg/g mitomycin C, the solutions also each contained 25 mg/g urea. At t=0 and after 5, 22 and 27 hours at room temperature (RT) with exclusion of light and in the refrigerator, the purity of the solutions was investigated according to process 2.

TABLE 14

"Stability of mitomycin C in 25 mg/g urea-containing solutions"

| | Mitomycin C purity* [%] | | |
|---|---|---|---|
| Conditions | t = 5 h | t = 22 h | t = 27 h |
| RT; with exclusion of light | 99.6 | 99.1 | 98.6 |
| 5° C.; with exclusion of light | 99.8 | 99.5 | 99.5 |

*HPLC determination by process 2; purity is defined as area of the mitomycin peak relative to the total area of all peaks in the HPLC chromatogram Even after more than one day's storage at room temperature, the purity of the solution is surprisingly high, which reflects the surprisingly high stability of the active substance in the solvent.

Example 9

Freeze-Drying of Solutions of Mitomycin C Containing Urea or Polyethylene Glycol (50 mg/g)

Solutions of mitomycin C in a mixture of 89 wt.-% tert.-butanol and 11 wt.-% water were prepared. As well as 3.33 mg/g mitomycin C, the solutions also each contained either 50 mg/g urea or PEG 4000. In each case, 6 g of these solutions was filled into small vials and freeze-dried in conventional manner. The lyophilisate cakes containing urea and PEG 4000 were firm and defect-free.

The lyophilisates were analysed for the purity of mitomycin C directly after their preparation (t=0) and after storage for 1 month (t=1 month) at 40° C. The results are presented in Table 15.

TABLE 15

"Stability of lyophilisates with urea and polyethylene glycol"

| Additive | Mitomycin purity * [%] | Reconstitution time |
|---|---|---|
| | t = 0; | |
| Urea | 99.65 | <<30 secs |
| PEG 4000 | 99.34 | <<30 secs |
| | t = 1 month at 40° C.; | |
| Urea | 99.89 | <<30 secs |
| PEG 4000 | 96.19 | <<30 secs |

* HPLC determination by process 2; purity is defined as area of the mitomycin peak relative to the total area of all peaks in the HPLC chromatogram Even after storage at an elevated temperature of 40° C., the lyophilisates produced had a high purity of mitomycin C, which reflects their very good stability.

Moreover, the lyophilisates could be completely reconstituted with isotonic saline solution in very much less than 30 secs.

Example 10

Freeze-Drying of Solutions of Mitomycin C Containing Urea (20 mg/g)

Solutions of mitomycin C in a mixture of 89 wt.-% tert.-butanol (TBA) and 11 wt.-% water were prepared. As well as 1.33 mg/g mitomycin C, the solutions also each contained 20 mg/g urea. In each case, 1.5 g of this solution was filled into small vials and freeze-dried in conventional manner. The lyophilisate cakes were firm and defect-free.

The lyophilisates were analysed for the purity of mitomycin C directly after their preparation (t=0). In addition, the reconstitution time was determined. The reconstitution was effected with isotonic saline solution to an end concentration of 1 mg/g mitomycin C. The results are presented in Table 16.

TABLE 16

"Characteristics of urea-containing lyophilisates"
t = 0

| Additive | Mitomycin C purity* [%] | Reconstitution time |
|---|---|---|
| Urea | 99.5 | <<30 secs |

*HPLC determination by process 2; purity is defined as area of the mitomycin peak relative to the total area of all peaks in the HPLC chromatogram The lyophilisates produced had a high purity of mitomycin C, which reflects the very good stability of the active substance during the process.

Moreover, the lyophilisates could be completely reconstituted with isotonic saline solution in very much less than 30 secs.

Example 11

Freeze-Drying of Solutions of Mitomycin C Containing Urea (25 mg/g)

Solutions of mitomycin C in a mixture of 89 wt.-% tert.-butanol (TBA) and 11 wt.-% water were prepared. As well as 1.67 mg/g mitomycin C, the solutions also each contained 25 mg/g urea. In each case, 1.2 g of this solution was filled into small vials and freeze-dried in conventional manner. The lyophilisate cakes with urea were firm and defect-free.

TABLE 17

"Urea-containing lyophilisates"
t = 0

| Additive | Mitomycin purity [%]* | Reconstitution time |
|---|---|---|
| Urea | 99.5 | <<30 secs |

*HPLC determination by process 2; purity is defined as area of the mitomycin peak relative to the total area of all peaks in the HPLC chromatogram The lyophilisates produced had a high purity of mitomycin C, which reflects the very good stability of the active substance during the process. Moreover, the lyophilisates could be completely reconstituted with isotonic saline solution in very much less than 30 secs.

Example 12

Mitomycin C in Tert.-Butanol/Water Mixture (95/5) with Mannitol (45 mg/g)

Solutions of mitomycin C in a mixture of 95 wt.-% tert.-butanol (TBA) and 5 wt.-% water were prepared. As well as 5 mg/g mitomycin C, the solutions also each contained 45 mg/g mannitol. In each case, 4.0 g of this solution was filled into small vials and freeze-dried in conventional manner. The lyophilisate cakes were firm and defect-free.

TABLE 18

"Mannitol-containing lyophilisate"
t = 0

| Additive | Mitomycin purity* [%]* | Reconstitution time |
|---|---|---|
| Mannitol | 99.6 | <<30 secs |

*HPLC determination by process 2; purity is defined as area of the mitomycin peak relative to the total area of all peaks in the HPLC chromatogram The lyophilisates produced had a high purity of mitomycin C, which reflects the very good stability of the active substance during the process. Moreover, the lyophilisates could be completely reconstituted with isotonic saline solution in very much less than 30 secs.

Example 13

Stability of Mitomycin Lyophilisates

Solutions of mitomycin C in a mixture of 89 wt.-% tert.-butanol (TEA) and 11 wt.-% water were prepared. As well as 3.33 mg/g mitomycin C, the solutions also each contained 50 mg/g urea. In each case, 6 [corresponds to 20 mg mitomycin C] or 12 g [corresponds to 40 mg mitomycin C] of these solutions was filled into small vials and freeze-dried in conventional manner. The lyophilisates obtained were examined at different times t=0, t=3 months and t=6 months at 40° C. and 75% relative humidity (r.h.).

The determination of the content of mitomycin C was performed by process 3 and that of the impurities content by process 4. The reconstitution was effected with 20 and 40 ml respectively of isotonic saline solution to an end concentration of 1 mg/ml.

TABLE 19

"Stability at 40° C. and 75% r.h. [20 mg mitomycin C]"

|  | t = 0 | t = 3 months | t = 6 months |
|---|---|---|---|
| Reconstitution time | 7 secs | 12 secs | 17 secs |
| Mitomycin C content* | 97.8% | 98.2% | 98.3% |
| Impurity albomitomycin C** | 0.29% | 0.20% | 0.26% |
| Sum of all impurities** | 0.29% | 0.55% | 0.61% |

*determination by process 3
**determination by process 4

TABLE 20

"Stability at 40° C. and 75% r.h. [40 mg mitomycin C]"

|  | t = 0 | t = 3 months | t = 6 months |
|---|---|---|---|
| Reconstitution time | 6 secs | 20 secs | 18 secs |
| Mitomycin C content* | 97.2% | 96.6% | 96.7% |
| Impurity albomitomycin C** | 0.32% | 0.22% | 0.21% |
| Sum of all impurities** | 0.32 | 0.55 | 0.58 |

*determination by process 3
**determination by process 4

Even after 6 months' storage at elevated temperature of 40° C. and elevated atmospheric humidity of 75% r.h., the lyophilisates produced contained only very small quantities of impurities. Moreover, the lyophilisates could be completely reconstituted with isotonic saline solution in very much less than 30 secs.

Example 14

Elevated End Concentration after Reconstitution

Solutions of mitomycin C in a mixture of 89 wt.-% tert.-butanol and 11 wt.-% water were prepared. As well as 3.33 mg/g mitomycin C, the solutions also each contained 50 mg/g urea. In each case, 6 g [corresponds to 20 mg mitomycin C] of these solutions was filled into small vials and freeze-dried in conventional manner. The lyophilisates obtained were reconstituted with 20 ml or 10 ml water for injection.

| Mitomycin C end concentration | Mitomycin C content* [%] | Description of the reconstituted solution |
|---|---|---|
| 1 mg/ml | 100.6 | Clear, free from visible particles |
| 2 mg/ml | 100.6 | Clear, free from visible particles |

*determination by process 3

The reconstituted solutions in water for injection had a high content of mitomycin C. The solutions were clear and free from visible particles.

The invention claimed is:

1. Process for the preparation of a freeze-dried pharmaceutical composition comprising mitomycin C, comprising freeze-drying a solution of mitomycin C, wherein the solution comprises a mixture of tert.-butanol and water, which mixture comprises 84 to 95 wt. % tert.-butanol.

2. Process according to claim 1, in which the solution comprises mitomycin C at a concentration of 0.1 to 500 mg per gram of the solution.

3. Process according to claim 1, in which the solution additionally comprises at least one additive selected from the group of urea, polyethylene glycol and mannitol.

4. Process according to claim 3, in which the solution comprises urea at a concentration of 1 to 200 mg per gram of the solution.

5. Process according to claim 3, in which the polyethylene glycol has an average molecular weight (number average) of 1000 to 8000 and preferably of 2000 to 8000.

6. Process according to claim 3, in which the solution comprises polyethylene glycol at a concentration of 1 to 200 mg/g.

7. Process according to claim 3, in which the solution comprises mannitol at a concentration of 1 to 200 mg/g.

* * * * *